United States Patent [19]

Casey, Jr.

[11] Patent Number: 4,601,582

[45] Date of Patent: Jul. 22, 1986

[54] SPECTROPHOTOMETER

[75] Inventor: William T. Casey, Jr., Chalfont, Pa.

[73] Assignee: Milton Roy Company, Ivyland, Pa.

[21] Appl. No.: 800,903

[22] Filed: Nov. 22, 1985

Related U.S. Application Data

[63] Continuation of Ser. No. 742,633, Jun. 10, 1985, abandoned, which is a continuation of Ser. No. 455,116, Jan. 3, 1983, abandoned.

[51] Int. Cl.[4] .................. G01J 3/51; G01N 21/03; G01N 21/33
[52] U.S. Cl. .................. 356/414; 250/373; 356/411
[58] Field of Search ............ 356/409, 410, 411, 414, 356/416, 418, 419, 436, 437, 440, 244, 246; 250/205, 373, 573, 576

[56] References Cited

U.S. PATENT DOCUMENTS

| | | | |
|---|---|---|---|
| 3,498,719 | 3/1970 | Wing et al. | 356/410 X |
| 4,066,362 | 1/1978 | Carter | 356/440 |
| 4,274,744 | 6/1981 | Chae et al. | 356/414 |

Primary Examiner—F. L. Evans
Attorney, Agent, or Firm—Woodcock Washburn Kurtz Mackiewicz & Norris

[57] ABSTRACT

A spectrophotometer is shown in which a deuterium lamp emits a plurality of frequencies of interest the beam passes through a filter for selecting the wavelength of the light desired to be incident onto the sample and then onto a beam splitting plate which diverts a relatively small friction of the beam to a first reference photocell. The remaining portion of the beam then is incident directly on a sample tube. The sample tube may be so designed that its transparent walls form a lens focusing the beam on the sample to be tested. The beam then passes through the further wall of the sample tube and is detected by a second testing photocell, the output of which may be compared to the output of the reference photocell to provide a signal indicative of the relative amplitude of the testing beam. The reference photocell may be used to insure that the intensity of the beam incident on the beam splitter remains constant over time so that values output by the testing photocell may be comparable to measurements taken at a later time, without the use of a reference sample for calibration purposes. A sample cell is provided which allows the use of the instrument of the invention in on-line applications in high pressure systems. A particularly preferred method of mounting the deuterium bulb is also shown.

7 Claims, 5 Drawing Figures

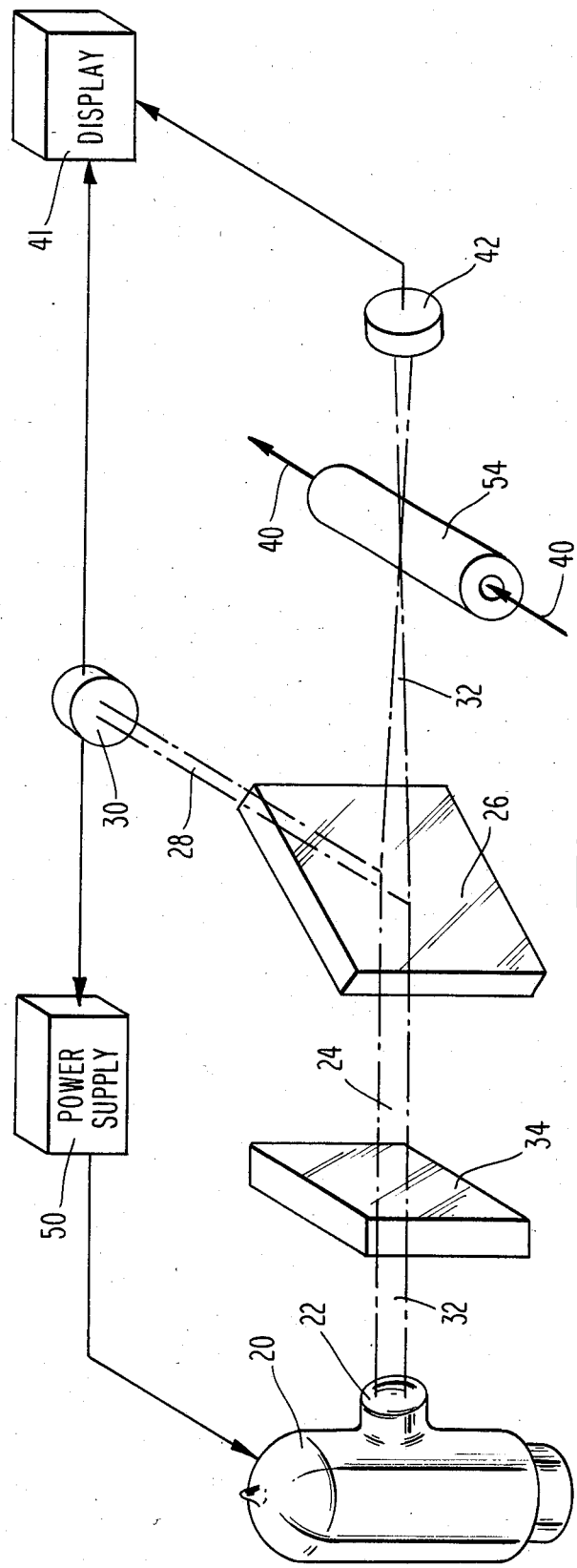
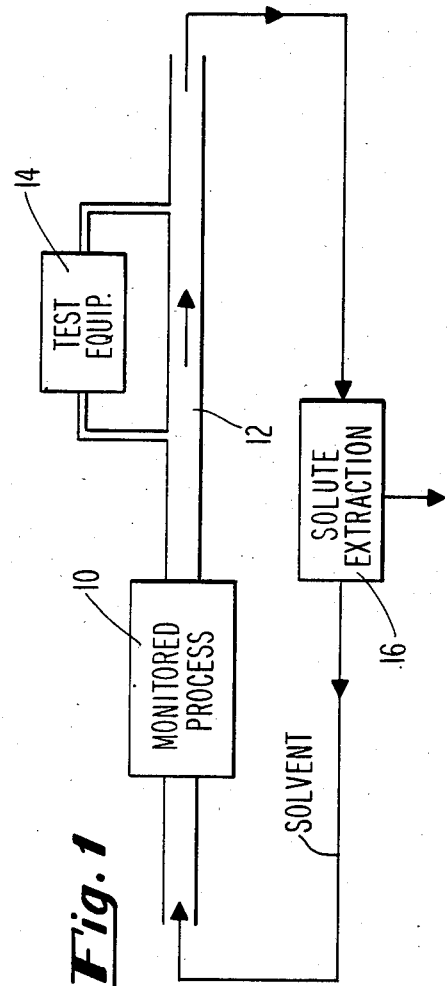
Fig. 1
Fig. 2

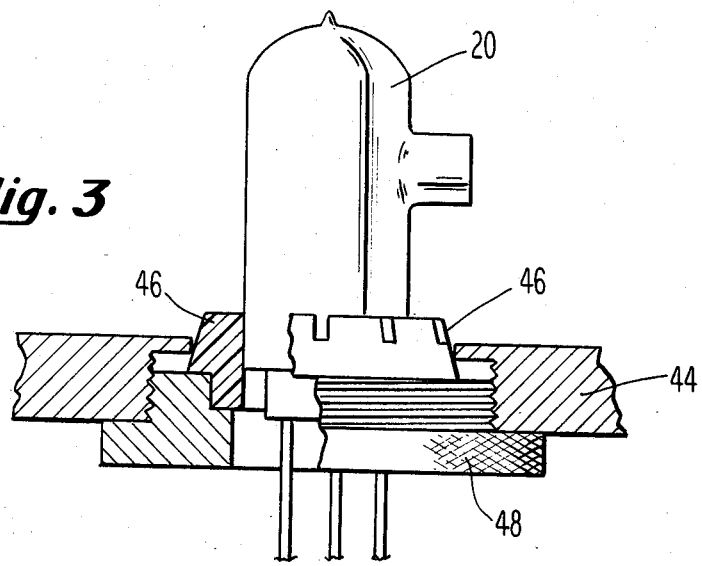
Fig. 3
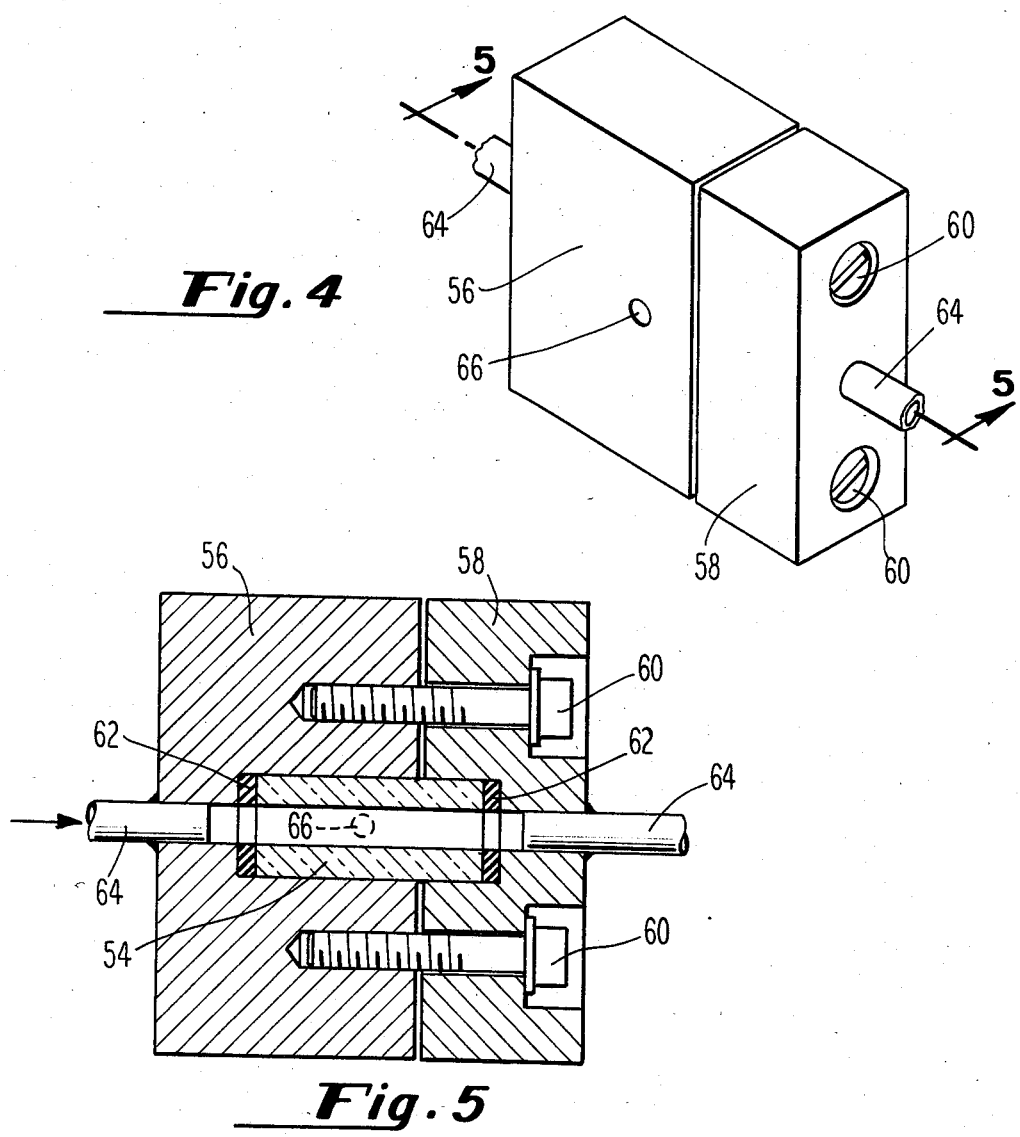
Fig. 4
Fig. 5

SPECTROPHOTOMETER

This is a continuation of application Ser. No. 742,633 filed June 10, 1985, now abandoned which in turn is a continuation of application Ser. No. 455,116 filed on Jan. 3, 1983 now abandoned.

FIELD OF THE INVENTION

This application relates to instruments for measuring absorption of light of given wavelength by a fluid sample under test. More particularly, the invention relates to an instrument for measuring absorption of light of selected wavelengths by a sample under test, specifically designed to be useful in optimization of laboratory processes and in the development of industrial scale processes of various types.

BACKGROUND OF THE INVENTION

For some years it has been known that meaningful laboratory analysis can be performed using instruments which emit light of a specific wavelength onto a gas or fluid sample and measure the amount of that light which passes through the sample to derive an indication of absorption. The absorption may be indicative of the presence of an impurity in a liquid under test, of solute in a solvent, of the color of the liquid, of the presence of solid matter suspended in the liquid, or the like. Numerous instruments for such applications are known. The art has well documented the wavelengths of light which are absorbed by various materials so that the absorption of light of a specific wavelength is indicative of the presence of a particular material in the sample under test; if the amount of incident light and transmitted light are compared, an indication of the amount of the absorptive material may be derived.

Many of the instruments found in the prior art relate to measurement of the absolute amount of light of a specified wavelength passed through a sample when compared with a reference sample. Accordingly, many of the instruments in the prior art show splitting of a single beam into two identical portions, passing one beam through the sample under test and one through a reference sample, and comparing the amount of light transmitted so as to generate a result proportional to the amount of light absorbing material in the sample under test. Such instruments are very useful when it is desired to generate an absolute value for absorption. However, they tend to be very specialized—for detection of absorption of a particular element or compound—inasmuch as the reference specimen against which the test sample is compared must be changed if the instrument is to be used with differing materials. Moreover, it is rather unusual that various materials tested absorb the same wavelength of light, so that if the same instrument is to be used for testing differing materials, not only must the sample chamber be cleaned carefully and a new reference sample provided, but also the source of light must be modified to emit a different wavelength. While systems have been shown in the prior art which show means for emission of varying wavelength light, they are not as simple or as inexpensive as would be desired. For example, the SpectroMonitor III made by the assignee of the present invention uses a deuterium lamp to emit light of a wide range of wavelengths and then uses a diffraction grating to select the particular wavelength of light which is incident on the sample. This system is workable, but the diffraction grating is expensive and must be operated by precision mechanical means which add complexity to the system. In order to select the wavelength of interest, it would be desirable to manufacture an instrument having the capability of the SpectroMonitor III but at lesser expense. Moreover, the SpectroMonitor III is an instrument of the type described above, i.e., one in which the beam is split into equal portions for irradiation of a sample of known constituency and the sample under test. The beam splitter used is a fiber optic device which is expensive to manufacture and accordingly adds unduly to the cost of the instrument. It would likewise therefore be desirable to eliminate this optical device.

As noted above, the instruments in the prior art tend to be designed to generate a objective value for the quantitative difference between a reference sample and a sample to be tested. Such instruments are useful in laboratories where analysis of a given sample is to be performed. However, there is another class of application of spectrophotometric instruments which is not addressed by this type of instrument. This class of applications involves development of industrial processes. Such development typically will take place in a laboratory scale operation where a variety of parameters are to be varied to select the optimum operating conditions for a given process. For example, there is at present a publicly felt desire for decaffeinated coffee wherein the caffeine is removed from the coffee using non-poisonous or non-carcinogenic solvents such as carbon dioxide. Processes are being developed all over the world for the removal of caffeine from coffee beans using supercritical carbon dioxide, i.e., carbon dioxide raised to a temperature and a pressure above its critical point, so that the gas behaves as a solvent. There are numerous variables in the supercritical solvent extraction process and it would be desirable to be able to vary them on a more or less continuous basis and to provide a continuous indication of the efficacy of the process at any given time. Accordingly, it would be desirable to provide an instrument which would provide a substantially instantaneous indication of the amount of caffeine in the supercritical $CO_2$ stream leaving the apparatus, so that an experimenter could make an adjustment to the process parameters and immediately see whether or not the efficiency of extraction had been improved. It will be recognized by those skilled in the art that such an instrument need not provide an absolute value of the amount of caffeine in the supercritical $CO_2$ stream, but merely provide an accurate indication of whether or not the amount had increased or decreased since the process parameter was changed.

As discussed above, most of the instruments in the prior art for spectrophotometric measurement have split the beam of incident light of given radiation into two equal parts so as to equally irradiate a sample to be tested and a reference sample. This is done in order to insure accuracy of the objective measurement provided by the photocell exposed to the radiation passing through the sample to be tested. However, splitting the beam into two parts means that the energy output by the lamp is split as well, which is undesirable in the case of darker, more absorptive samples as then more amplification is necessary to turn the lower photocell output into a meaningful output signal. It will be appreciated by those skilled in the art that as the photocell output signal drops, it gets more and more closely related in amplitude to the noise inherent in any electrical system. Accordingly, it would be desirable, for a given lamp, to direct as much of its beam as possible on the sample so as to generate a larger output signal, thus raising the effective signal-to-noise ratio of the system.

Another deficiency of prior art spectrophotometric measurements when applied to modern processes now under development such as supercritical carbon dioxide extraction of caffeine from coffee beans is that these processes typically take place under very high pressures, e.g., 10,000 psi. If an instrument is to be interposed "on line" in the system, it must be capable of withstanding such pressures. No instrument is known to the inventor which satisfies this requirement. Instead, previous spectrophotometric instruments require that a sample be taken and transferred to the instrument at a lower pressure, which greatly complicates the process and renders an on-line instrument unfeasible. This, in turn, renders easy optimization of the process parameters by obtaining an instantaneous read-out of the effective variation of a process parameter impossible.

OBJECTS OF THE INVENTION

Accordingly, it is an object of the invention to provide an improved spectrophotometer both in terms of utility in on-line testing of process streams and in terms of cost.

It is a further object of the invention to provide a spectrophotometer which has the capability of varying the wavelength of light incident on a particular sample.

It is a further object of the invention to provide a spectrophotometer which is capable of withstanding extremely high pressures.

It is a further object of the invention to provide a spectrophotometer in which a major part of the light emitted by the bulb irradiating the sample falls on the sample and not on a reference sample, whereby the signal-to-noise ratio of the output signal is enhanced.

Yet another object of the invention is to provide a spectrophotometer comprising means for irradiating a sample with a plurality of wavelengths with a single lamp, while avoiding complex mechanical/optical constructions such as high precision adjustment of the position of a diffraction grating in the beam path.

Yet another object of the invention is to provide a spectrophotometer in which the use of fiber optic devices for beam splitting is avoided.

SUMMARY OF THE INVENTION

The present invention satisfies the above-mentioned objects of the invention and needs of the art by its provision of a spectrophotometer in which a deuterium lamp emits a plurality of frequencies of interest onto a filter for selecting the wavelength of the light designed to be incident onto the sample A beam splitting plate then diverts a relatively small fraction of the beam to a first reference photocell. The remaining portion of the beam then is incident directly on a sample tube. The sample tube may be so designed that its transparent walls form a lens focusing the beam on the sample to be tested. The beam then passes through the further wall of the sample tube and is detected by a second testing photocell, the output of which may be compared to the output of the reference photocell to provide a signal indicative of the relative amplitude of the testing beam. The reference photocell may be used to insure that the intensity of the beam incident on the beam splitter remains constant over time so that values output by the testing photocell may be comparable to measurements taken at a later time, without the use of a reference sample for calibration purposes. A sample cell is provided which allows the use of the instrument of the invention in on-line applications in high pressure systems. A particularly preferred method of mounting the deuterium bulb is also a feature of the instrument of the invention.

BRIEF DESCRIPTION OF THE DRAWINGS

The invention will be better understood if reference is made to the accompanying drawings, in which:

FIG. 1 shows a schematic view of use of the instrument of the invention in a process being developed;

FIG. 2 shows a perspective view of the instrument of the invention;

FIG. 3 shows a cross-sectional view of the preferred method of mounting the deuterium bulb used;

FIG. 4 shows a perspective view of the fluid sample test cell; and

FIG. 5 is a cross-sectional view of the fluid sample test cell.

DESCRIPTION OF THE PREFERRED EMBODIMENTS

As mentioned above, FIG. 1 is a schematic view showing how the instrument of the invention can be used in a process plant under development, such as a supercritical carbon dioxide decaffeination plant. The process to be monitored at 10 will typically have an output stream 12; in the decaffeination example, the output stream is supercritical $CO_2$ solvent having some amount of caffeine entrained therein. A portion of this output stream 12 is passed to the testing equipment of the invention at 14 and returned to the output line. In some cases, the process will be continuous as shown. There, for example, the caffeine would be extracted at 16 and the $CO_2$ returned to the input side of the extraction process 10. By putting the apparatus of the invention on line, in contrast to prior art methods in which the sample was removed and analyzed at some later time, the effect of a change in the process parameters can be noted immediately. This is of significant advantage when optimizing processes which have a large number of process variables.

FIG. 2 shows in perspective the main elements of the spectrophotometric system of the invention. A deuterium bulb 20, for example, that manufactured by the Hamamatsu Company under the model number L1626 outputs a beam of light 32 comprising a plurality of frequencies at an output port 22. As is understood, light is selectively absorbed as a function of wavelength by varying materials. Accordingly, if an instrument is to be utilized for measurement of the absorption by these plural materials, the beam output by the lamp must include all the frequency components of interest or complex means must be provided for alteration of the frequency of the light, such as phosphors or the like. The deuterium lamp 20 mentioned above has such a wide range of frequencies. The beam 32 is passed through a filter 34 which absorbs all but the frequency which is absorbed by the material of interest in the specimen to be tested. The filtered beam 24 is then split in a beam splitter 26, such as the model Corning 7940 manufactured by CVI Laser Corporation Dec. 17, 1982 and a comparatively small fraction of the beam is passed at 28 to a first photocell 30. The remaining portion of the filtered beam 32 then passes into a sample chamber which may comprise a glass tube 54 connected to have the sampled fluid flow therethrough, as indicated at 40.

The beam which passes through the sample is detected by a second photocell 42.

The outputs of the photocells 30 and 42 may be utilized in numerous ways. For example, the photocell 30 which outputs a signal representative of the amount of light incident thereon without passing through the sample can be used to maintain the output of the lamp 20 constant over long periods of time, so that measurements made by the second photocell 42 can be compared with other measurements. Alternatively, the output of one photocell can be divided into another giving a proportional output which can be used to provide a display 41, for direct comparison to products of similar measurements made at other times. In this way any variation in the intensity of the lamp 20 over time does not affect the system. It will clearly be desirable that the photocells are identical, so that their characteristics vary equally with respect to aging, ambient temperature and the like. In the preferred embodiment, the photocells used were Model No. HUV-1000B sold by EG&G Electro-Optics which incorporate amplifiers in the photodiode chip itself, further simplifying the circuitry required.

It will be appreciated by those skilled in the art that the beam splitter 26 mentioned is of a type which is comparatively inexpensive particularly when compared to the fiber optic types which split beams into equal proportions and that it only splits off a comparatively small fraction of the beam for direction onto the first photocell 30. The remainder of the beam is then incident on the sample contained in the sample tube 38. It is highly desirable that such a major fraction of the incident beam be used in the measurement because this effectively increases the signal-to-noise ratio of the absorption measurement made.

As discussed above, it is desirable that the instrument of the invention be useful for absorption measurements of a variety of materials many of which absorb different wavelengths. In order that the instrument can be adapted to be used with such differing materials it is only necessary to replace the filter 34. For example, the caffeine of interest in the supercritical carbon dioxide decaffeination process discussed above exhibits strong absorption of ultraviolet light having a wavelength in the 254 nanometer region. A filter suitable for absorbing substantially all light output by the deuterium bulb but 254 nm radiation is available from the Corion Corporation under Model No. P6-254-25D. Accordingly, to change the instrument from one for measuring absorption of ultraviolet light by caffeine to measurement of another substance, one need only insure that the sample tube 38 is cleansed, by passing a solvent or the like therethrough, and by replacing the filter 34 as necessary with one which passes only the frequency absorbed by the new material to be analyzed. This is in distinct contrast to the method of the prior art, referred to above, in which a diffraction grating is used to reflect only selected wavelengths onto a beam splitter prior to division for incidence on a reference sample and a sample under analysis. Not only is the diffraction grating expensive, but the mechanical linkages which are necessary to insure its proper alignment are very complex and sensitive to damage, are unduly affected by thermal expansion, and the like. Note also that placement of the filter prior to the beam splitter ensures that both photocells "see" light of the same relative frequency components, thus removing yet another obstacle to accurate measurement.

The current practice of the art in mounting deuterium bulbs is to use spring and set screw arrangements for holding the lamp in a vertical position. Such arrangements are unduly complex and inaccurate. FIG. 3 shows a preferred method for avoiding these problems. The deuterium bulb 20 is mounted in an orifice in a base plate 44 by means of a serrated Teflon ring 46 which is mounted around the bulb. The ring 46 is then tigthened on the bulb by the coaction of a threaded ring 48 and threads in the base plate 44. The leads for the bulb may be passed through a hole in the ring 48 and thence to a power supply 50, as indicated schematically in FIG. 2.

As mentioned above, the decaffeination process using supercritical carbon dioxide requires extremely high pressurized carbon dioxide. As also noted above, it is desirable that the instrument of the invention be an on-line instrument capable of more or less instantaneously outputting a representation of any change in the amount of caffeine removed by the carbon dioxide solvent upon modification of one of the operating parameters. This can only be done if the fluid cell, i.e., the chamber within which the fluid is contained for exposure to the ultraviolet light output by the deuterium bulb 20, is capable of withstanding these extremely high pressures. FIGS. 4 and 5 show an improved sample cell which is so capable. It comprises a sample tube 54 which may be formed of a silicate glass compressed by mating metal blocks 56 and 58 which may be made of aluminum or the like, which are held together by screws 60. Upon tigthening of screws 60, the ends of the tube are sealed O-rings or similar static seals 62. The tubes 64 which make connections to the remainder of the system must, of course, be sealed as well; in a preferred embodiment, stainless steel tubes 64 are used, and these are brazed to the aluminum blocks 56 and 58. An optical orifice 66 is provided through both sides of block 56 through which the beam 32 of the deuterium lamp passes. As shown schematically in the drawing of FIG. 2, the tube 54 provides a focusing effect to the beam. In a successfully tested embodiment of the invention, the tube 54 was formed of quartz glass sold by the Wilmad Glass Company. The tube was of inside diameter 0.128" and outside diameter 0.312". The only area at which the tube is unsupported is in the area of the view port 66 through which the beam passes; this port should be no larger than about 0.094" in diameter for use up to 10,000 psi.

Those skilled in the art will recognize that there has been described a spectrophotometer for use in systems where an absolute measurement of the absorption of an incident light beam by a particular compound of interest is not required, such that simultaneous irradiation by the incident beam of the specimen under test and of a reference sample can be avoided. Instead, the instrument of the invention is useful in systems where a change in the absorption is to be noted, and in particular, in systems where such an indication is needed in an on-line system so as to enable ready optimization of a number of process variables in a process under development.

Those skilled in the art will also recognize that the instrument of the invention is readily adaptable to measurement of absorption of a wide variety of compounds, because the sample chamber is very simply cleaned and furthermore because all that need be done to alter the wavelength of the incident light is to change a single filter, as the deuterium lamp supplies all frequencies generally of interest in such processes.

It will be appreciated as well that the use of the plate-type beam splitter permits most of the incident light to fall on the sample; very little is diverted to the reference photocell, so that accordingly the signal-to-noise ratio of the test is substantially improved. Use of a second photodiode for adjustment of the relative lamp bulb intensity adds little complexity to the system yet provides repeatability in measurements made over long periods of time.

Finally, it will also be recognized that numerous other embodiments of the invention beside the exemplary one shown and described above are possible, and that accordingly this description should not be considered as a limitation on the scope of the invention but merely as illustrative thereof. The scope of the invention is to be measured accordingly by the following claims.

I claim:

1. A spectrophotometer for continuously monitoring an effect of changing parameters in an on-line process stream under exremely high pressure, comprising:
   means for emitting a first beam of light having a plurality of wavelengths;
   means, optically coupled to said emtiting means, for filtering said first beam of light and transmitting a second beam of light consisting of a preselected wavelength;
   means for disproportionately splitting said second beam of light into a first and second component, whereby said first component has a substantially greater intensity than said second component;
   means, optically coupled to said splitting means, for measuring the intensity of said second component;
   a sample cell, optically coupled to said splitting means, said sample cell comprising a pair of rigid cell members releasably joined together to form an inner cavity of substantially cylindrical shape, one of said cell members having bored therethrough an optical orifice having a preselected diameter and an axis extending transversely through the axis of said cavity, a substantially transparent tube contained within and supported by said cavity, said tube having a preselected inside diameter and wall thickness, a pair of static seal members, each attached at a respective end of said tube thereby forming a pressure seal between said tube and said cell members, and input and discharge means in communication with said tube for providing a flowpath through which the process stream may be sampled, wherein the ratio of the wall thickness of said tube to the diameter of said optical orifice is approximately 2:1 and wherein the ratio of the diameter of said optical orifice to the inside diameter of said tube does not exceed 0.75, whereby said first component is transmitted through said tube via said optical orifice; and
   photodiode means, optically coupled to said sample cell and sensitive to light having said preselected wavelength, for producing a signal indicative of the amount of light absorbed by the process stream within said tube.

2. The apparatus of claim 1 wherein said emitting means is comprised of a deuterium lamp.

3. Apparatus for on-line measurement of high pressure processes to determine the absorption of radiation by a sample under test comprising:
   means for emission of a beam of radiation;
   means for disproportionately dividing said beam of radiation into a first and second component, whereby said first component has a substantially greater intensity than said second component;
   means for measurement of the amount of said second component of said radiation;
   means for total absorption of a first selected frequency-defined portion of said radiation while permitting passage of another preselected frequency-defined portion of said radiation;
   a sample cell for containing a sample in the optical path of said first component of said radiation, wherein said sample cell comprises a glass tube confined within and supported by at least two metallic blocks members, one of said at least two block members having a hole formed therethrough for the passage of said first component of said radiation, said hole having a diameter not to exceed 0.094 inches, said glass tube sealed to said block members by static seals confined within said block members; and
   means for measurement of the amount of said first component of said radiation not absorbed by said sample.

4. The apparatus of claim 3 wherein said emission means is a deuterium lamp emitting radiation over a wide range of wavelengths.

5. The apparatus of claim 3 wherein said division means comprises a beam splitting plate.

6. The apparatus of claim 3 wherein said absorbing means comprises an optical filter.

7. The apparatus of claim 3 wherein said means for measurement of the amount of said second component of said radiation is a photocell.

* * * * *